US00PP20845P2

(12) United States Plant Patent
Catt

(10) Patent No.: US PP20,845 P2
(45) Date of Patent: Mar. 16, 2010

(54) ***PEROVSKIA* PLANT NAMED 'LISSLITT'**
(50) Latin Name: *Perovskia atriplicifolia*
Varietal Denomination: LISSLITT

(76) Inventor: Peter Catt, Liss Forest Nurseries, Greatham, Liss, Hampshire GU 33 6HA (GB)

( * ) Notice: Subject to any disclaimer, the term of this patent is extended or adjusted under 35 U.S.C. 154(b) by 0 days.

(21) Appl. No.: 12/317,728

(22) Filed: Dec. 29, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—Annette H Para
(74) *Attorney, Agent, or Firm*—Penny J. Aguirre

(57) ABSTRACT

A new cultivar of *Perovskia* plant named 'LISSLITT', characterized by its compact plant habit, its foliage that is highly dissected and silver-green in color, and its stiff, upright flowering stems with an abundance of flowers.

2 Drawing Sheets

Botanical classification: *Perovskia atriplicifolia.*
Variety denomination: 'LISSLITT'.

BACKGROUND OF THE INVENTION

The present invention relates to a new and distinct cultivar of *Lamium* plant, botanically known as *Perovskia atriplicifolia* 'LISSLITT' and will be referred to hereinafter by its cultivar name, 'LISSLITT'. The new cultivar of *Perovskia* is a hardy herbaceous perennial grown for landscape use.

'LISSLITT' resulted from a breeding project by the Inventor at his nursery in Liss, Hampshire, United Kingdom with the goal of developing a more compact cultivar with stiff, upright flowering stems. The Inventor self-pollinated *Perovskia atriplicifolia* 'Blue Spire' (not patented) in 1999, the collected seeds were sown in 2001 and the new cultivar was selected as a single unique plant from the resulting seedlings in 2002.

Asexual reproduction of the new cultivar was first accomplished by the Inventor by means of stem cuttings in 2003 in Liss, Hampshire, United Kingdom. The characteristics of the new cultivar have been found to be stable and reproduced true to type in successive generations.

SUMMARY OF THE INVENTION

The following traits have been repeatedly observed over a period of six years and represent the characteristics of the new cultivar. These attributes in combination distinguish 'LISSLITT' as a new and unique cultivar of *Perovskia.*

1. 'LISSLITT' exhibits a compact plant habit.
2. 'LISSLITT' exhibits foliage that is highly dissected and silver-green in color.
3. 'LISSLITT' exhibits flowering stems that are stiff and held upright.
4. 'LISSLITT' exhibits an abundance of flowers per stem.

The parent plant, 'Blue Spire', differs from 'LISSLITT' being taller in height, in having foliage that is less dissected, less silver in color with longer internodes and in having fewer flowering stems, a more open plant habit, and smaller flower calyces. The closest comparison cultivar is 'Little Spire' (U.S. Plant Pat. No. 11,643). 'Little Spire' differs from 'LISSLITT' in being smaller in stature, in having fewer flowering stems and inflorescences that are more open with less flowers.

BRIEF DESCRIPTION OF THE DRAWINGS

The accompanying colored photographs illustrate the overall appearance and distinct characteristics of the new *Perovskia.* The photographs were taken of two year-old plants of 'LISSLITT' as grown outdoors in three-liter containers in Liss, Hampshire, United Kingdom.

The photograph in FIG. 1 illustrates the consistent plant habit of 'LISSLITT'.

Figure 2:
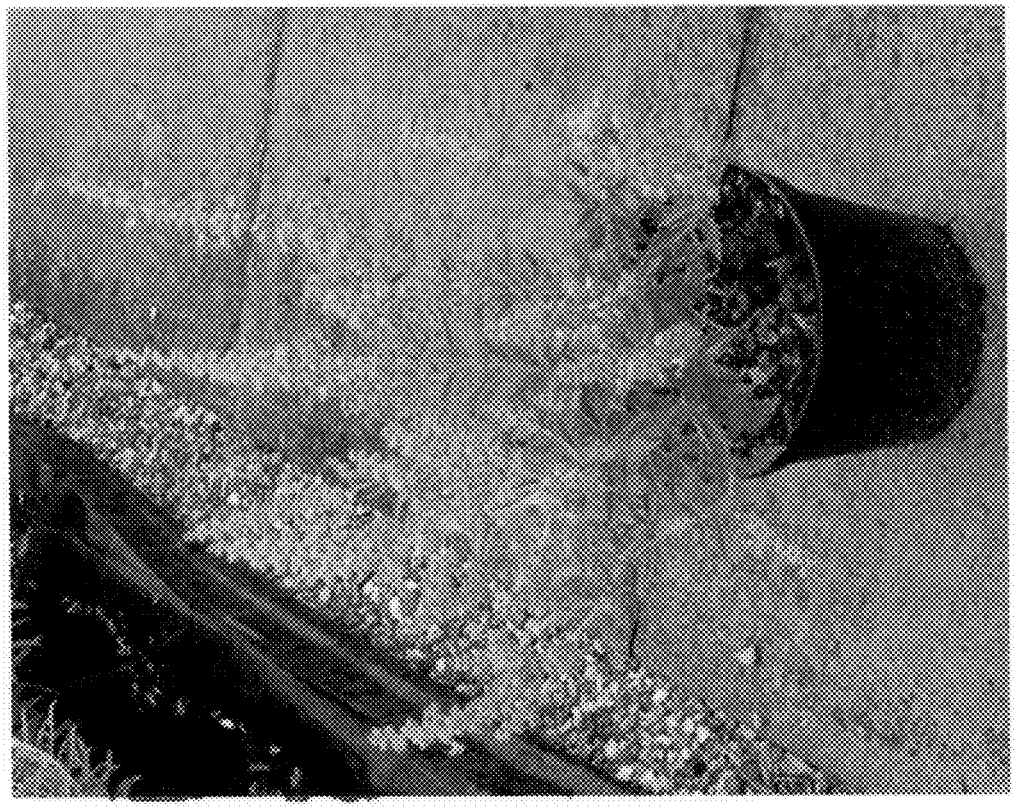

The photograph in FIG. 2 provides a view of a single plant of 'LISSLITT' in full bloom.

Figure 1:
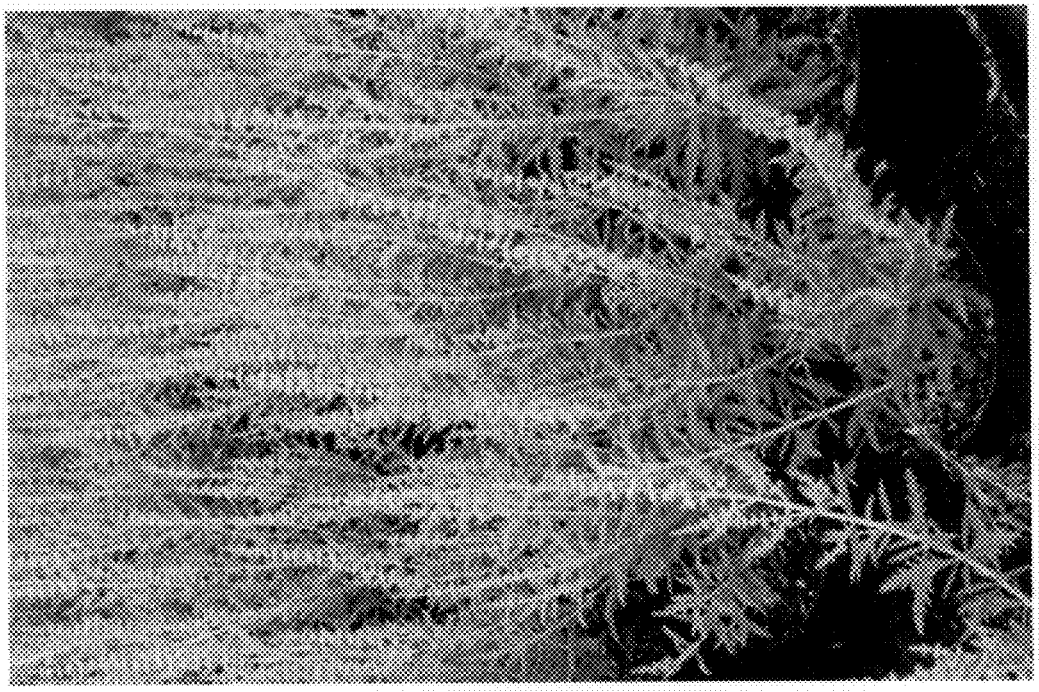
Figure 3:
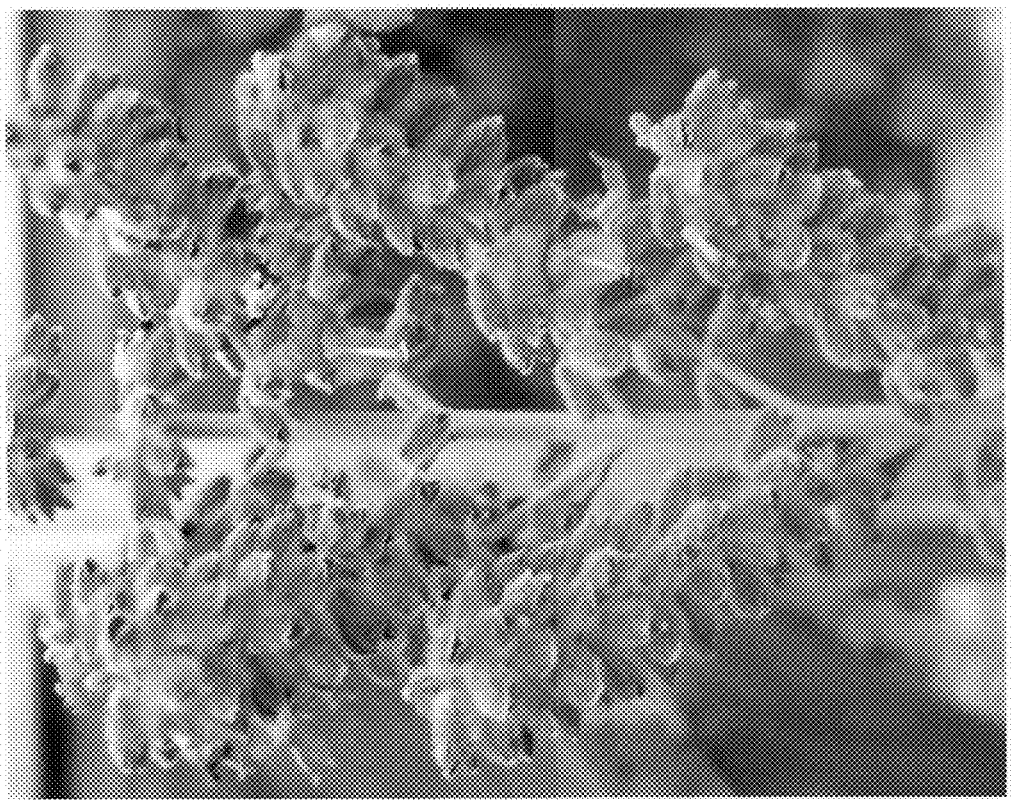

The photograph in FIG. 3 provides a close up view of the flowers of 'LISSLITT'.

The colors in the photograph may differ slightly from the color values cited in the detailed botanical description, which accurately describe the colors of the new *Perovskia.*

DETAILED BOTANICAL DESCRIPTION

The following is a detailed description of the new cultivar as observed for six years in Georgia with the detailed botanical data collected from a plant grown in a two year-old plant as grown outdoors in three liter containers in Liss, Hampshire, United Kingdom. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—July to September in southern United Kingdom with calyces remaining attractive for another several weeks.

*Plant type.*—Deciduous semi-woody sub-shrub.

*Plant habit.*—Compact, initially bushy and becoming erect with maturity.

*Height and width.*—Reaches about 75 cm in height and 15 to 25 cm in width in the first year and 75 to 100 cm in height and 25 to 30 cm in width in the second year.

*Hardiness.*—U.S.D.A. Zones 5 to 9.

*Diseases and pests.*—No susceptibility or resistance to diseases or pests has been observed.

*Root description.*—Fibrous.

*Propagation.*—Stem cuttings; root initiation occurs in 14 to 21 days at a temperature of 20° C.

*Growth rate.*—Moderately vigorous.

Stem description:

*Shape.*—Square.

*Stem color.*—188C.

*Stem size.*—Average of 3 mm in diameter and 60 cm in length.

*Stem surface.*—Densely felted with stellate and simple hairs.

*Branching habit.*—Basal branches.

Foliage description:

*Leaf division.*—Simple.

*Leaf arrangement.*—Opposite.

*Leaf shape.*—Elliptic to broadly lanceolate.

*Leaf size.*—Average of 4.5 cm in length and 1.5 cm in width.

*Leaf base.*—Cuneate.

*Leaf apex.*—Acute.

*Leaf margin.*—Deeply and irregularly dissected with some dissections having an addition small tooth at base.

*Leaf venation.*—Pinnate, 137D in color on upper and lower surface.

*Leaf attachment.*—Petiolate.

*Leaf surface.*—Upper and lower surface; pubescent with scattered stellate and simple hairs.

*Leaf internode length.*—Average of 1.5 cm.

*Leaf color.*—Upper surface; N137C, lower surface; 137D.

*Petiole.*—Average of 4 mm in length and 2 mm in length, 138D in color, surface is pubescent with scattered stellate and simple hairs.

*Foliage fragrance.*—Aromatic.

Inflorescence description:

*Inflorescence type.*—Terminal branched panicle of verticillicasters of bilabiate flowers.

*Lastingness of inflorescence.*—Individual flowers about 6 days, not persistent.

*Inflorescence size and arrangement.*—27 to 35 cm in length with 6 to 10 lateral branches held at an angle of 75 to 90° to peduncle that are 5 to 10 cm in length and an average of 1.8 cm in width.

*Flower type.*—Bilabiate.

*Flower number.*—Up to 12 per verticillaster, over 100 per inflorescence.

*Flower fragrance.*—Aromatic.

*Flower buds.*—Ovoid in shape, about 6 mm in length and 3 mm in diameter, N87B in color.

*Flower size.*—About 1.3 cm in length and about 8 mm in diameter.

*Peduncles.*—30 to 40 cm in length from base of first flower to apex, an average of 2 mm in width, 188A in color, surface is densely felted with stellate and simple hairs, an internode length of about 12 mm between verticillicasters.

*Pedicels.*—About 1 mm in length and <1 mm in width, 188A in color, surface is pubescent.

*Calyx.*—Tubular, about 7 mm in length and 3 mm in width, persistent for a few weeks after petals drop.

*Sepals.*—5, fused at base with apex free, triangular in shape and <1 mm in length and width, 194C in color and tinged with N88C (especially towards apex), surface is pubescent with tangled glandular hairs about 0.5 mm in length, base is fused, acute apex, entire margin.

*Petals.*—5 lobes arranged in 2 lips fused into tube at base, tube; about 6 mm in length and 1 to 2 mm in width, color 155A at base becoming 94D at apex, all lobes; entire margins, smooth surface, upper lip; 4-lobed, held upright to 90° to tube to slightly bent backwards, about 6 mm in length and 8 mm in width, 94B in color, lower lip; 1 lobed, ovate in shape, about 6 mm in length and 5 mm in width, 94B to 94C in color.

Reproductive organs:

*Gynoecium.*—1 pistil, style is about 5 mm in length, <1 mm in width and 155A in color and flushed with 94D towards apex, stigma is bi-fid, about 1 mm in width and 94C in color, ovary is superior, 4-lobed, <0.5 mm in diameter and about 145D in color.

*Androecium.*—2 stamens, adnate to corolla and exserted, filaments are about 1 cm in length, <1 mm in width and 155A in color flushed with 94D towards apex, anthers are about 1 mm in length and 94C in color, pollen is moderate in quantity and 11D in color.

*Seed.*—Ovoid in shape, <0.5 mm in length and 0.5 mm in width, about 200A in color.

It is claimed:

1. A new and distinct variety of *Perovskia* plant named 'LISSLITT' as described and illustrated herein.

* * * * *